United States Patent [19]

Skidmore et al.

[11] Patent Number: 4,963,564
[45] Date of Patent: Oct. 16, 1990

[54] PHENETHANOLAMINE DERIVATIVES

[75] Inventors: Ian F. Skidmore, Welwyn; Alan Naylor, Royston; Harry Finch, Letchworth; Lawrence H. C. Lunts, Broxbourne; Ian B. Campbell, Dane End, all of England

[73] Assignee: Glaxo Group Ltd., London, England

[21] Appl. No.: 230,359

[22] Filed: Aug. 10, 1988

[30] Foreign Application Priority Data

Aug. 11, 1987 [GB] United Kingdom ................ 8718940

[51] Int. Cl.$^5$ ................. C07D 213/36; C07D 215/14; A61K 31/44; A61K 31/47
[52] U.S. Cl. .................................. 514/311; 514/334; 546/176; 546/264
[58] Field of Search ................ 546/176, 264; 514/311, 514/334

[56] References Cited

U.S. PATENT DOCUMENTS 4,379,166  4/1983  Neustadt et al. ..................... 424/324

FOREIGN PATENT DOCUMENTS

| 0178919 | 4/1986 | European Pat. Off. |
| 0223410 | 5/1987 | European Pat. Off. |
| 0220878 | 6/1987 | European Pat. Off. |
| 2140800 | 12/1984 | United Kingdom |
| 2159151 | 11/1985 | United Kingdom |
| 2152842 | 7/1986 | United Kingdom |

Primary Examiner—David B. Springer
Attorney, Agent, or Firm—Morgan & Finnegan

[57] ABSTRACT

The invention provides compounds of the general formula (I)

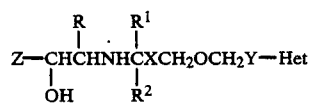

(I)

and physiologically acceptable salts and solvates thereof, wherein Z represents the group

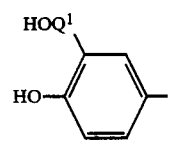 (a)

(wherein $Q^1$ represents a straight or branched $C_{1-3}$alkylene group),

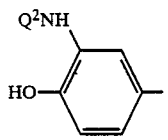 (b)

(where $Q^2$ represents a group $R^5CO-$, $R^5NHCO-$, $R^5R^6NSO_2-$ or $R^7SO_2-$, where $R^5$ and $R^6$ each represent a hydrogen atom or a $C_{1-3}$alkyl group, and $R^7$ represents a $C_{1-3}$alkyl group), or

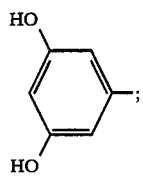 (c)

X represents a bond, or a $C_{1-7}$alkylene, $C_{2-7}$alkenylene or $C_{2-7}$alkynylene chain, and Y represents a bond, or a $C_{1-6}$alkylene, $C_{2-6}$alkenylene or $C_{2-6}$alkynylene chain with the proviso that the sum total of carbon atoms in the chains X and Y is not more than 10;

R represents a hydrogen atom or $C_{1-3}$alkyl group;

$R^1$ and $R^2$ each represent a hydrogen atom or a $C_{1-3}$alkyl group; with the proviso that the sum total of carbon atoms in $R^1$ and $R^2$ is not more than 4; and Het represents a benzoheteroaryl or a monocyclic heteroaryl group wherein the heteroaryl group is 5 or 6 membered and contains 1, 2 or 3 hetero atoms, one of which is a nitrogen atom and the other(s) is (are) nitrogen, oxygen or sulphur atom(s), and the group Het may optionally be substituted by one or two groups selected from $C_{1-4}$alkyl, $C_{1-4}$alkoxy, hydroxy, halogen, $-NR^3R^4$ and $-COR^8$; where $R^3$ and $R^4$ each represent a hydrogen atom or a $C_{1-4}$alkyl group or $-NR^3R^4$ forms a saturated heterocyclic amino group which has 5-7 ring members and optionally contains in the ring one or more atoms selected from $-O-$ or $-S-$ or a group $-NH-$ or $-N(CH_3)-$; and $R^8$ represents hydroxy, $C_{1-4}$alkoxy or $-NR^3R^4$.

The compounds have a stimulant action at $\beta_2$-adrenoreceptors and may be used in the treatment of diseases associated with reversible airways obstruction such as asthma and chronic bronchitis.

4 Claims, No Drawings

PHENETHANOLAMINE DERIVATIVES

This invention relates to phenethanolamine derivatives having a stimulant action at $\beta_2$-adrenoreceptors, to processes for their preparation, to pharmaceutical compositions containing them and to their use in medicine.

Phenethanolamine derivatives have previously been described as bronchodilators having stimulant activity at $\beta$-adrenoreceptors.

Thus, for example, UK Patent Specification Nos. 2140800A and 2159151A describe phenethanolamine derivatives possessing an hydroxyalkyl substituent on the phenol ring, of the general structure

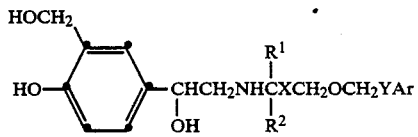

in which $R^1$ and $R^2$ each represent hydrogen or $C_{1-3}$alkyl; X represents a $C_{1-7}$ alkylene, $C_{2-7}$alkenylene or $C_{2-7}$ alkynylene chain; Y represents a $C_{1-6}$alkylene, $C_{2-6}$alkenylene or $C_{2-6}$alkynylene chain; and Ar represents a phenyl group optionally substituted by one or more of a variety of specific substituents.

UK Patent Specification No. 2162842A describes phenethanolamine derivatives possessing a sulphonamido substituent on the phenol ring of the general structure.

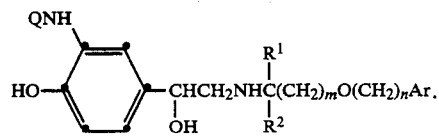

in which $R^1$ and $R^2$ each represent hydrogen or $C_{1-3}$alkyl; m is an integer from 2 to 8; n is an integer from 1 to 7; Ar is an optionally substituted phenyl group; and Q represents a group $R^3CO-$, $R^3NHCO-$, $R^3R^4NSO_2-$ or $R^5SO_2-$ where $R^3$ and $R^4$ each represent a hydrogen atom or a $C_{1-3}$alkyl group and $R^5$ represents a $C_{1-4}$alkyl group.

UK Patent Specification No. 2160863A and European Patent Application No. 0223410A2 describe, inter alia, phenethanolamine derivatives in which the phenyl ring is substituted by two hydroxyl groups to give resorcinol derivatives of the general structure

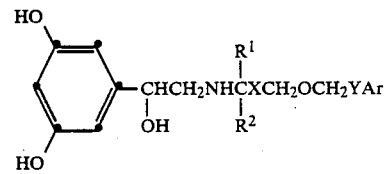

in which $R^1$ and $R^2$ each represent hydrogen or $C_{1-3}$alkyl; X represents a $C_{1-7}$alkylene, $C_{2-7}$alkenylene or $C_{2-7}$alkynylene chain; Y represents a $C_{1-6}$alkylene, $C_{2-6}$alkenylene or $C_{2-6}$alkynylene chain; and Ar is an optionally substututed phenyl group.

We have now found a novel group of compounds which differ structurally from those of UK Patent Specifications Nos. 2140800A, 2159151A, 2162842A and 2160863A, and European Patent Application No. 0223410A2, and which have a desirable and useful profile of activity. Thus the present invention provides compounds of the general formula (I)

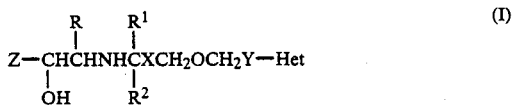

and physiologically acceptable salts and solvates (e.g. hydrates) thereof, wherein Z represents the group

(where $Q^1$ represents a straight or branched $C_{1-3}$ alkylene group),

(where $Q^2$ represents a group $R^5CO-$, $R^5NHCO-$, $R^5R^6NSO_2-$ or $R^7SO_2-$, where $R^5$ and $R^6$ each represent a hydrogen atom or a $C_{1-3}$ alkyl group, and $R^7$ represents a $C_{1-3}$ alkyl group), or

X represents a bond, or a $C_{1-7}$ alkylene, $C_{2-7}$ alkenylene or $C_{2-7}$ alkynylene chain, and Y represents a bond, or a $C_{1-6}$ alkylene, $C_{2-6}$ alkenylene or $C_{2-6}$ alkynylene chain with the proviso that the sum total of carbon atoms in the chains X and Y is not more than 10;

R represents a hydrogen atom or a $C_{1-3}$ alkyl group;

$R^1$ and $R^2$ each represent a hydrogen atom or a $C_{1-3}$ alkyl group, with the proviso that the sum total of carbon atoms in $R^1$ and $R^2$ is not more than 4; and Het represents a benzoheteroaryl or a monocyclic heteroaryl group wherein the heteroaryl group is 5 or 6 membered and contains 1, 2 or 3 hetero atoms, one of which is a nitrogen atom and the other(s) represent nitrogen, oxygen or sulphur atom(s), and the group Het may optionally be substituted by one or two groups selected from $C_{1-4}$ alkyl, $C_{1-4}$ alkoxy, hydroxy, halogen, $-NR^3R^4$ and $-COR^8$; where $R^3$ and $R^4$ each represent a hydrogen atom or a $C_{1-4}$ alkyl group or $-NR^3R^4$ forms a saturated heterocyclic amino group which has 5-7 ring members and optionally contains in the ring one or more atoms selected from $-O-$ or $-S-$ or a group $-NH-$ or $-N(CH_3)-$; and $R^8$ represents hydroxy, $C_{1-4}$ alkoxy or $-NR^3R^4$.

It will be appreciated that the compounds of general formula (I) possess one or more asymmetric carbon atoms. The compounds according to the invention thus include all enantiomers, diastereoisomers and mixtures thereof, including racemates. Compounds in which the carbon atom in the

group is in the R configuration are preferred.

In the definition of general formula (I), the term alkenylene includes both cis and trans structures.

In the general formula (I), the chain X may be for example a bond, —CH$_2$—, —(CH$_2$)$_2$—, —(CH$_2$)$_3$—, —(CH$_2$)$_4$—, —(CH$_2$)$_5$—, —(CH$_2$)$_6$—, —CH$_2$C≡C—, —(CH$_2$)$_2$CH=CH—, —(CH$_2$)$_2$C≡C—, —CH=CHCH$_2$—, —CH=CH(CH$_2$)$_2$— or —CH$_2$C≡CCH$_2$—. The chain Y may be for example a bond, —CH$_2$—, —(CH$_2$)$_2$—, —(CH$_2$)$_3$—, —(CH$_2$)$_4$—, —(CH$_2$)$_5$—, —(CH$_2$)$_6$—, CH=CH—, —C≡C—, —CH$_2$CH=CH— or —CH$_2$C≡C—.

Preferably the total number of carbon atoms in the chains X and Y is 4 to 10 inclusive. Compounds wherein the sum total of carbon atoms in the chains X and Y is 5, 6, 7, 8 or 9 are particularly preferred.

A further preferred group of compounds of formula (I) that wherein the sum total of carbon atoms in the chains X and Y is 7, 8 or 9, and especially preferred compounds are those wherein X represents the group —(CH$_2$)$_4$— and Y represents the group —(CH$_2$)$_3$— or —(CH$_2$)$_5$.

In the compounds of formula (I), R, R$^1$ and R$^2$ may each be, for example, methyl, ethyl, propyl or isopropyl groups. If one of R$^1$ and R$^2$ is a propyl or isopropyl group, the other is a hydrogen atom or a methyl group. R, R$^1$ and R$^2$ are each preferably a hydrogen atom or a methyl group.

A preferred group of compounds are those in which R represents a hydrogen atom.

Another preferred group of compounds are those wherein R$^1$ and R$^2$ are both hydrogen atoms, or R$^1$ is a hydrogen atom and R$^2$ is a C$_{1-3}$ alkyl group, particularly a methyl group, or R$^1$ is a methyl group and R$^2$ is a methyl group.

In the compounds of formula (I), Q$^1$ may be, for example, —CH$_2$—,

—(CH$_2$)$_2$— or —(CH$_2$)$_3$—. A preferred group of compounds are those in which
Q$^1$ represents —CH$_2$—.

Q$^2$ may represent for example HCO—, CH$_3$CO—, H$_2$NCO—, (CH$_3$)$_2$NSO$_2$— or, more preferably, CH$_3$SO$_2$—.

A preferred group of compounds of formula (I) are those in which Z represents the group

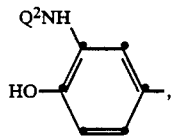

where Q$^2$ represents R$^7$SO$_2$— and R$^7$ represents a C$_{1-3}$ alkyl (e.g. methyl) group.

The group Het is attached to the rest of the molecule through any available position in the heteroaryl ring. Any substituent(s) in the group Het may be at any available position(s) in the benzene and/or the heteroaryl rings. Preferably Het represents a group selected from pyridyl, pyrimidinyl, pyrazinyl, triazinyl, thiazolyl, quinolinyl, benzimidazolyl, benzothiazolyl and benzoxazolyl.

A particularly preferred group of compounds of formula (I) is that in which Het represents a pyridyl or quinolinyl group.

When the group Het is substituted by one or two halogen atoms, these may be chlorine, fluorine or bromine. When —NR$^3$R$^4$ represents a saturated heterocyclic amino group, this may be, for example, a pyrrolidino, piperidino, hexamethyleneimino, piperazino, N-methylpiperazino, morpholino, homomorpholino or thiamorpholino group.

Preferred compound according to the invention are

N-[2-hydroxy-5-[1-hydroxy-2-[[6-[[6-(2-pyridinyl)hexyl]oxy]hexyl]amino]ethyl]phenyl]methanesulphonamide, N-[2-hydroxy-5-[1-hydroxy-2-[[6-[4-(2-quinolinyl)butoxy]hexyl]amino]ethyl]phenyl]methanesulphonamide, 4-hydroxy-α$^1$-[[[6-[[6-(2-pyridinyl)hexyl]oxy]hexyl]amino]methyl]-1,3-benzenedimethanol, N-[2-hydroxy-5-[1-hydroxy-2-[[6-[[6-(2-quinolinyl)hexyl]oxy]hexyl]amino]ethyl]phenyl]methanesulphonamide, and their physiologically acceptable salts and solvates.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, benzenesulphonates, p-toluenesulphonates, naphthalenesulphonates, methanesulphonates, sulphamates, ascorbates, salicylates, acetates, diphenylacetates, triphenylacetates, adipates, fumarates, succinates, lactates, glutarates, gluconates, tricarballylates, hydroxy-naphthalenecarboxylates e.g. 1-hydroxy- or 3-hydroxy-2-naphthalenecarboxylates, or oleates. The compounds may also form salts with suitable bases where appropriate. Examples of such salts are alkali metal (e.g. sodium and potassium) and alkaline earth metal (e.g. calcium or magnesium) salts, and salts with organic bases (e.g. triethylamine).

The compounds according to the invention have a stimulant action at β$_2$-adrenoreceptors, which furthermore is of a particularly advantageous profile. The stimulant action was demonstrated in the isolated trachea of the guinea-pig, where compounds were shown to cause relaxation of contractions induced by PGF$_{2α}$ or electrical stimulation. A prolonged duration of action has also been observed.

The compounds according to the invention may be used in the treatment of diseases associated with reversible airways obstruction such as asthma and chronic bronchitis.

The compounds according to the invention are also indicated as useful for the treatment of inflammatory and allergic skin diseases, congestive heart failure, depression, premature labour, glaucoma, and in the treatment of conditions in which there is an advantage in lowering gastric acidity, particularly in gastric and peptic ulceration.

The invention accordingly further provides compounds of formula (I) and their physiologically acceptable salts and solvates for use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in for example capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration by bolus injection or continuous infusion. Formulations for injection may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.005 mg to 100 mg, which may be conveniently administered in one or two doses. The precise dose employed will of course depend on the age and condition of the patient and on the route of administration. Thus a suitable dose for administration by inhalation is 0.005 mg to 20 mg, for oral administration is 0.02 mg to 100 mg, and for parenteral administration is 0.01 mg to 2 mg for administration by bolus injection and 0.01 mg to 25 mg for administration by infusion.

The compounds according to the invention may be prepared by a number of processes. In the following description, Z, X, Y, Het, R, $R^1$ and $R^2$ are as defined for general formula (I) unless otherwise specified. In the preparation of both intermediates and end-products the final step in the reaction may be the removal of a protecting group. Suitable protecting groups and their removal are described in general process (3) below.

In one general process (1), a compound of general formula (I) may be prepared by alkylation. Conventional alkylation procedures may be used.

Thus, for example, in one process (a), a compound of general formula (I) in which $R^1$ is a hydrogen atom may be prepared by alkylation of an amine of general formula (II)

(II)

(wherein $R^9$ is a hydrogen atom or a protecting group and $R^{10}$ is a hydrogen atom) followed by removal of any protecting group where present.

The alkylation (a) may be effected using an alkylating agent of general formula (III):

(III)

(wherein L is a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform, at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that $R^{10}$ is a hydrogen atom or a group convertible thereto under the reaction conditions, with a compound of general formula (IV):

$$R^2COXCH_2OCH_2Y\text{—Het} \qquad (IV)$$

in the presence of a reducing agent, followed when necessary by removal of any protecting groups.

Examples of suitable $R^{10}$ groups convertible into a hydrogen atom are arylmethyl groups such as benzyl, 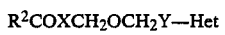 α-methylbenzyl and benzhydryl.

Suitable reducing agents include hydrogen in the presence of a catalyst such as platinum, platinum oxide, palladium, palladium oxide, Raney nickel or rhodium, on a support such as charcoal, using an alcohol, e.g. ethanol or methanol, or an ester e.g. ethyl acetate, or an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres.

Alternatively when one or both of $R^9$ and $R^{10}$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (II) where $R^9$ and $R^{10}$ are each hydrogen atoms is used, the intermediate imine of formula (V) may be formed:

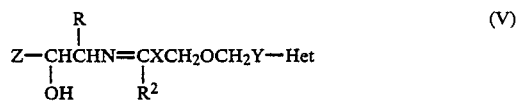

(V)

Reduction of the imine using the conditions described above, followed, where necessary, by removal of any protecting groups, gives compound of general formula (I).

In another general process (2) compounds of formula (I) may be prepared by reducing an intermediate of general formula (IV):

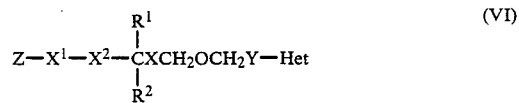

(VI)

wherein at least one of $X^1$, $X^2$, X and Y represents a reducible group and the other(s) take the appropriate meaning as follows, which is $X^1$ is —CH(OH)—, $X^2$ is —CHRNR$^9$— (where $R^9$ represents a hydrogen atom or a protecting group), and X and Y are as defined in formula (I), followed where necessary by removal of any protecting groups.

Suitable reducible groups include those wherein $X^1$ is a group

$X^2$ is a group —CHRNR$^{11}$— (wherein $R^{11}$ represents a group convertible to hydrogen by catalytic hydrogenation, for example an arylmethyl group such as benzyl, benzhydryl or α-methylbenzyl).

The reduction may be effected using reducing agents conveniently employed for the reduction of ketones or protected amines.

Thus, for example, when $X^1$ in general formula (VI) represents a

group this may be reduced to a —CH(OH)— group using hydrogen in the presence of a catalyst such as platinum, platinum oxide, palladium, palladium oxide, Raney nickel or rhodium, on a support such as charcoal, using an alcohol e.g. ethanol, an ester e.g. ethyl acetate, an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres. Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in an appropriate solvent, such as an alcohol e.g. methanol or ethanol, or an ether such as tetrahydrofuran, or a halogenated hydrocarbon such as dichloromethane.

When $X^2$ in general formula (VI) represents a —CHRNR$^{11}$— group this may be reduced to a —CHRNH— group using hydrogen in the presence of a catalyst as described above.

Where it is desired to use a protected intermediate of general formula (VI) it is particularly convenient to use a protecting group $R^9$ which is capable of being removed under the reducing conditions, for example hydrogen and a catalyst, thus avoiding the need for a separate deprotection step. Suitable protecting groups of this type include arylmethyl groups such as benzyl, benzhydryl and α-methylbenzyl.

In the above reduction process, and also in the preparation of intermediates, care must be taken when using hydrogen and a catalyst in the preparation of products in which X and/or Y represent alkenylene or alkynylene groups, and where a hydride reducing agent is used and end-products are required in which $Q^2$ represents the group $R^5CO$—.

In a further process (3) compounds of formula (I) may be prepared by deprotecting an intermediate of general formula (VII)

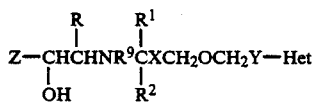 (VII)

wherein $R^9$ is a protecting group, and/or at least one of the hydroxy group(s) in Z is protected, and/or the group Het contains a protecting group.

The protecting group may be any conventional protecting group as described for example in "Protective Groups in Organic Chemistry", by Theodora Greene (John Wiley and Sons Inc, 1981). Thus, for example, hydroxyl groups may be protected by arylmethyl groups such as benzyl, diphenylmethyl or triphenylmethyl, by acyl groups such as acetyl, or as tetrahydropyranyl derivatives. Examples of suitable amino protecting groups include arylmethyl groups such as benzyl, α-methylbenzyl, diphenylmethyl or triphenylmethyl, and acyl groups such as acetyl, trichloroacetyl or trifluoroacetyl.

The deprotection to yield a compound of general formula (I) may be effected using conventional techniques. Thus for example arylmethyl groups may be removed by hydrogenolysis in the presence of a metal catalyst (e.g. palladium on charcoal). Tetrahydropyranyl groups may be cleaved by hydrolysis under acidic conditions. Acyl groups may be removed by hydrolysis with an acid such as a mineral acid e.g. hydrochloric acid, or a base such as sodium hydroxide or potassium carbonate, and a group such as trichloroacetyl may be removed by reduction with, for example, zinc and acetic acid.

Intermediates of formula (VI) for use in the reduction process (2) in which $X^1$ is the group

may be prepared by reaction of a haloketone of formula (VIII)

 (VIII)

(where Hal represents a halogen atom e.g. bromine) with an amine of formula (IX)

 (IX)

(where $R^9$ is a hydrogen atom or a group convertible thereto by catalytic hydrogenation).

The reaction may be effected in a cold or hot solvent, for example tetrahydrofuran, tert-butyl methyl ether, dioxan, chloroform, dichloromethane, dimethylformamide, acetonitrile, a ketone such as butanone or methylisobutylketone, or an ester such as ethyl acetate, preferably in the presence of a base such as diisopropylethylamine, sodium carbonate or other acid scavenger such as propylene oxide.

Intermediates of general formula (VI) in which $X^1$ is the group

may be reduced to the corresponding intermediate in which $X^1$ is the group —CH(OH)— using for example a metal hydride such as sodium borohydride in a solvent e.g. ethanol, methanol and/or tetrahydrofuran.

Amines of formula (II) and haloketones of formula (VIII) are either known compounds or may be prepared by methods analogous to those described for the preparation of known compounds.

Suitable methods for preparing intermediates of formulae (III), (IV) and (IX) are described in UK Patent Specifications Nos. 2140800A and 2159151A and in the exemplification included hereinafter.

In the general processes described above, the compound of formula (I) obtained may be in the form of a salt, conveniently in the form of a physiologically acceptable salt. Where desired, such salts may be converted to the corresponding free bases using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol, e.g. methanol, ethanol or isopropanol.

Physiologically acceptable salts may also be prepared from other salts, including other physiologically acceptable salts, of the compounds of general formula (I), using conventional methods.

When a specific enantiomer of a compound of general formula (I) is required, this may be obtained by resolution of a corresponding racemate of a compound of general formula (I) using conventional methods.

Thus, in one example an appropriate optically active acid may be used to form salts with the racemate of a compound of general formula (I). The resulting mixture of isomeric salts may be separated for example by fractional crystallisation, into the diastereoisomeric salts from which the required enantiomer of a compound of general formula (I) may be isolated by conversion into the required free base.

Alternatively, enantiomers of a compound of general formula (I) may be synthesised from the appropriate optically active intermediates using any of the general processes described herein.

Specific diastereoisomers of a compound of formula (I) may be obtained by conventional methods for example, by synthesis from an appropriate asymmetric starting material using any of the processes described herein, or by conversion of a mixture of isomers of a compound of general formula (I) into appropriate diastereoisomeric derivatives e.g. salts which then can be separated by conventional means e.g. by fractional crystallisation.

The following examples illustrate the invention. Temperatures are in °C. 'Dried' refers to drying using sodium sulphate. Unless otherwise stated, thin layer chromatography (t.l.c.) was carried out on silica and flash column chromatography (FCC) on silica (Merck 9385) using one of the following solvent systems:A-toluene:ethanol:0.88 ammonia, B-toluene:ethanol:triethylamine. The following abbreviations are used: THF-tetrahydrofuran, DMF - dimethylformamide, BTPC-bis(triphenylphosphine)palladium (II) chloride, TAB-tetra-n-butyl ammonium hydrogen sulphate, DEA-N,N-diiospropylethylamine.

Intermediate 1

2-[6-[(6-Bromohexyl)oxy]hexyl]pyridine

2-Pyridinehexanol (4.88 g), 1,6-dibromohexane (12.6 ml), 12.5M aqueous sodium hydroxide (25 ml) and TAB (0.45 g) were stirred rapidly at room temperature for 7 h. The mixture was diluted with water (60 ml) and extracted with diethyl ether (3×60 ml). The combined organic extracts were washed with water (60 ml) and brine (60 ml), dried and concentrated to give an oil which was purified by FCC eluting with diethyl ether-hexane (0:1→1:1) to give the title compound as a colourless oil (4.52 g), t.l.c. (ether-hexane 1:1) Rf 0.25.

Intermediate 2

N-[6-[[6-(2-Pyridinyl)hexyl]oxy]hexyl]benzenemethanamine

2-[6-[(6-Bromohexyl)oxy]hexyl]pyridine (4.99 g) was added dropwise to benzylamine (22 ml) at 140° C. under nitrogen. The solution was stirred at 140° for 1 h and distilled under vacuum to remove benzylamine. The residue was partitioned between ethyl acetate (300 ml) and 8% aqueous sodium bicarbonate (200 ml). The dried organic layer was concentrated and the residual oil was purified by FCC eluting with ethyl acetate-triethylamine (100:1) to give the title compound as a pale yellow oil (4.65 g), t.l.c. (ethyl acetate+few drops triethylamine) Rf 0.23.

Intermediate 3

4-(2-Quinolinyl)-3-butynol

A mixture of 2-bromoquinoline (0.44 g), 3-butynol (0.2 ml), N,N-dicyclohexylamine (0.46 ml), BTPC (30 mg), copper (I) iodide (5 mg) and acetonitrile (10 ml) was stirred at 22° for 5 h. Ether (50 ml) was added, and the mixture filtered and evaporated in vacuo. The residue was purified by FCC eluting with ether followed by ether-methanol (19:1), to afford the title compound as a colourless solid (0.41 g). A small sample recrystallised from ethyl acetate-hexane had m.p. 89°-91°.

Intermediate 4

2-Quinolinebutanol 4-(2-Quinolinyl)-3-butynol (2.53 g) was hydrogenated over pre-reduced 10% palladium on charcoal (50% aqueous paste, 0.6 g) in ethanol (100 ml) at room temperature and pressure. The reaction mixture was filtered through hyflo and evaporated in vacuo to afford the title compound as a colourless semi-solid (2.50 g), t.l.c. (diethyl ether), Rf 0.20.

Intermediate 5

2-[4-[(6-Bromohexyl)oxy]butyl]quinoline

A mixture of 2-quinolinebutanol (2.56 g), 1,6-dibromohexane (5 ml), dichloromethane (2 ml), TAB (150 mg) and 50% aqueous sodium hydroxide (5 ml) was stirred at room temperature for 18 h. Ether (40 ml) was added and the organic phase separated, washed with water (20 ml), brine (20 ml), dried and evaporated in vacuo to an oil. The oil was purified by chromatography over a column of silica (Merck 60, Art. 7734). Elution with hexane and hexane-ether (9:1) followed by hexane-ether (1:1) afforded the title compound (2.12 g) as a colourless oil, t.l.c. (diethyl ether), Rf 0.50.

Intermediate 6

2-[2-[(6-Bromohexyl)oxy]ethyl]quinoline

A mixture of 2-quinolineethanol (1.00 g), 1,6-dibromohexane (4 ml), TAB (100 mg), 50% aqueous sodium hydroxide (4 ml) and dichloromethane (3 ml) was stirred at room temperature for 40 h, then diluted with water (40 ml) and ether (25 ml). The organic phase was washed with water (20 ml), dried and evaporated in vacuo. The residual oil was purified by FCC eluting with hexane followed by hexane-ether (9:1) and ether, to give the title compound (1.18 g) as a pale yellow oil, t.l.c. (diethyl ether) Rf 0.44.

Intermediate 7

3-[3-[(6-Bromohexyl)oxy]propyl]pyridine

A mixture of 3-pyridinepropanol (10 g), 1,6-dibromohexane (40 ml) 50% (w/v) sodium hydroxide (40 ml) and TAB (1.0 g) was stirred at room temperature for 3 h, water (150 ml) was added and the mixture was extracted with ether (2×200 ml). The organic extracts were washed with water and brine, dried and concentrated to an oil which was purified by FCC eluting with hexane→hexane-ether (1:1), to give the title compound as a yellow oil (11.0 g), t.l.c. (hexane-ether 1:1) Rf 0.16.

Intermediate 8

2-[3-[(6-Bromohexyl)oxy]propyl]pyridine

A mixture of 2-pyridinepropanol (15.8 g), 1,6-dibromohexane (60 ml), 50% (w/v) sodium hydroxide (60 ml) and TAB (1.5 g) was stirred at room temperature for 5 h. Water (200 ml) was added and the mixture was extracted with ether (2×200 ml). The organic extracts were washed with water and brine, dried and concentrated to an oil which was purified by FCC eluting with hexane→hexane-ether (1:1) to give the title compound as a colourless oil (18.1 g), t.l.c. (hexane-ether 1:1) Rf 0.19.

Intermediate 9

N-[6-[3-(2-Pyridinyl)propoxy]hexyl]benzenemethanamine

2-[3-[(6-Bromohexyl)oxy]propyl]pyridine (17.0 g) was added to benzylamine (50 ml) at 140° under nitrogen. After 1 h at 140° the reaction mixture was cooled and partitioned between 2N sodium hydroxide (250 ml) and ether (250 ml). The organic layer was washed with water and brine, dried and concentrated to a yellow oil. The excess benzylamine was removed by distillation to give the title compound as a yellow oil (18.5 g), t.l.c. (System A 80:20:2) Rf 0.42.

Intermediate 10

1-[4-Hydroxy-3-(hydroxymethyl)phenyl]-2-[(phenylmethyl)[6-[3-(2-pyridinyl)propoxy]hexyl]amino]ethanone A solution of 2-bromo-1-[4-hydroxy-3-(hydroxymethyl)phenyl]ethanone (2.45 g), N-[6-[3-(2-pyridinyl)propoxy]hexyl]benzenemethanamine (3.26 g) and DEA (2.6 g) in THF (25 ml) was left at room temperature for 48 h. The precipitate was removed by filtration, the solvent was evaporated and the residual red oil was purified by FCC eluting with System B (95:5:1→90:10:1) to give the title compound as a pale yellow oil (3.32 g), t.l.c. (System A 80:20:1) Rf 0.21.

Intermediate 11

1-[4-Hydroxy-3-(hydroxymethyl)phenyl]-2-[(phenylmethyl)[6-[[6-(2-pyridinyl)hexyl]oxy]hexyl]amino]ethanone A solution of 2-bromo-1-[4-hydroxy-3-(hydroxymethyl)phenyl]ethanone (1.00 g), N-[6-[[6-(2-pyridinyl)hexy]oxy]hexyl]benzenemethanamine (1.5 g) and DEA (1.58 g) in THF (20 ml) was left to stand for 24 h. The reaction mixture was filtered and the filtrate was concentrated to give an oil which was purified by FCC eluting with System B (95:5:1), to give the title compound as a yellow oil (1.96 g), t.l.c. (System A 80:20:2)) Rf 0.33.

Intermediate 12

3,5-Bis(phenylmethoxy)-α-[[(phenylmethyl)[6-[[6-(2-pyridinyl)hexyl]-oxy]hexyl]amino]methyl]benzenemethanol A solution of 1-[3,5-bis(phenylmethoxy)phenyl]-2-bromoethanone (1.76 g) in dry DMF (15 ml) was added dropwise to a solution of N-[6-[[6-(2-pyridinyl)hexyl]oxy]hexyl]benzenemethanamine (1.58 g) and DEA (0.56 g) in dry DMF (15 ml) under nitrogen. The mixture was stirred at room temperature for 4.5 h, and the solvent was evaporated. Sodium borohydride (1.75 g) was added portionwise to the ice-cooled solution of the residue in ethanol (40 ml) under nitrogen and the reaction mixture was stirred at room temperature for 16 h and concentrated. The residue was partitioned between ethyl acetate (70 ml) and water (70 ml), the organic layer was washed with brine (70 ml), dried and concentrated to give an oil which was purified by FCC eluting with ethyl acetatehexane-triethylamine (25:75:1) to give the title compound as a colourless oil (2.00 g), t.l.c. (ethyl acetate-hexane (1:2)+ few drops triethylamine) Rf 0.19.

Intermediate 13

6-[(6-Bromohexyl)oxy]-1-hexyne

A mixture of 5-hexyn-1-ol (5 g), 1,6-dibromohexane (37.29 g), TAB (1 g) and 50% sodium hydroxide solution (20 ml) was stirred under nitrogen for 22 h. The mixture was diluted with water (100 ml) and extracted with diethyl ether (2×150 ml). The combined organic extracts were dried and evaporated in vacuo to give an oil. Purification by FCC eluting with hexane followed by hexane:ether (95:5) gave the title compound as a colourless oil. (7.7 g), t.l.c. (hexane:ether 2:1) Rf 0.80.

Intermediate 14

2-[6-[(6-Bromohexyl)oxy]-1-hexynyl]quinoline

A mixture of 2-bromoquinoline (3.00 g), 6-[(6-bromohexyl)oxy]-1-hexyne (3.77 g), BTPC (90 mg), copper (I) iodide (11 mg), and dicyclohexylamine (2.79 g) in acetonitrile (35 ml) was stirred at room temperature under nitrogen for 20 h. The mixture was diluted with ether (90 ml), filtered and the filtrate evaporated in vacuo to give a brown oil. Purification by FCC eluting with hexane:ether (4:1→2:1) gave the title compound as a brown oil (4.25 g), t.l.c. (hexane:ether 2:1) Rf 0.22.

Intermediate 15

2-[6-[(6-Bromohexyl)oxy]hexyl]quinoline

A solution of 2-[6-[(6-bromohexyl)oxy]-1-hexynyl]quinoline (2.29 g) in ethanol (120 ml) was hydrogenated at room temperature and pressure over pre-reduced 10% palladium on carbon (1 g) for 20 min. The catalyst was removed by filtration through hyflo and the filtrate evaporated in vacuo to a brown oil. Purification by FCC eluting with hexane-ether (2:1) gave the title compound as a pale brown oil (1.70 g), t.l.c. (hexane:ether 2:1) Rf 0.21.

Intermediate 16

(E)-Methyl 3-[3-(phenylmethoxy)pyridin-2-yl]-2-propenoate

Crude 3-(phenylmethoxy)-2-pyridinecarboxaldehyde (30 g) and carbomethoxymethylenetriphenylphosphorane (55 g) in acetonitrile (800 ml) were stirred at reflux overnight. The solution was evaporated onto silica (Merck 9385) which was then purified by FCC eluting with ethyl acetate to give the product contaminated with triphenylphosphine oxide. This crude product was triturated with ether and the triturate was evaporated to an oil which was chromatographed on a column of silica (Merck 9385) eluting with cyclohexane followed by cyclohexane/ethyl acetate (4:1) to give the title compound as a yellow oil (270 g), t.l.c. (cyclohexane/ethyl acetate/triethylamine 80:20:1) Rf 0.17.

Intermediate 17

3-(Phenylmethoxy)-2-pyridinepropanol

A solution of (E)-methyl 3-[3-(phenylmethoxy)-2-pyridinyl]-2-propenoate (12.0 g) in dry ether (100 ml) was added to a stirred suspension of lithium aluminium hydride (5 g) in ether (200 ml) under nitrogen. The mixture was heated at reflux overnight and treated successively with water (5 ml), 2N sodium hydroxide (10 ml) and water (100 ml). Ethyl acetate (250 ml) was added and the mixture was filtered. The solution was washed with water and brine, dried and concentrated to an oil which was purified by FCC eluting with cyclohexane/ethyl acetate/triethylamine (80:20:1) followed by ethyl acetate/triethylamine (99:1) to give the title compound as a pale orange oil (1.4 g), t.l.c. (ethyl acetate/triethylamine 99:1) Rf 0.21.

Intermediate 18

2-[3-[(6-Bromohexyl)oxy]propyl]-3-(phenylmethoxy)pyridine

A mixture of 3-(phenylmethoxy)-2-pyridinepropanol (1.4 g), 1,6-dibromohexane (4 ml), 40% aqueous sodium hydroxide (4 ml) and TAB (100 mg) was stirred vigorously for 6 days. Water (10 ml) was added and the mixture was extracted with ether (3×10 ml). The ether extracts were washed with water and brine, dried and concentrated to an oil which was purified by FCC eluting with cyclohexane followed by cyclohexane/ethyl acetate (4:1) to give the title compound as an orange oil (1.0 g) t.l.c. (cyclohexane/ethyl acetate 4:1) Rf 0.25.

Intermediate 19

N-[6-[3-[3-(Phenylmethoxy)-2-pyridinyl]propoxy]hexyl]benzene methanamine

2-[3-[(6-Bromohexyl)oxy]propyl]-3-(phenylmethoxy)pyridine (1.0 g) was added to benzylamine (3 ml) at 120° under nitrogen. After stirring for 2 h, the solution was cooled and added to water (10 ml) and 2N hydrochloric acid (10 ml). The aqueous mixture was basified with sodium carbonate and then extracted with ethyl acetate (3×50 ml). The ethyl acetate was evaporated and the excess benzylamine was removed by distillation at reduced pressure to leave the title compound as a red oil (810 mg), t.l.c. (ethyl acetate/triethylamine 99:1) Rf 0.13.

Intermediate 20

1-[4-Hydroxy-3-(hydroxymethyl)phenyl]-2-[[6-[3-[3-(phenylmethoxy)-2-pyridinyl]propoxy]hexyl](phenylmethyl)amino]ethanone A solution of 2-bromo-1-[4-hydroxy-3-(hydroxymethyl)phenyl]ethanone (460 mg), N-[6-[3-[3-(phenylmethoxy)-2-pyridinyl]propoxy]hexyl]benzenemethanamine (800 mg) and DEA (485 mg) in THF (15 ml) was left at room temperature overnight. Water (30 ml) and ether (30 ml) were added, the phases were separated, and the organic layer was re-extracted with ether (50 ml). The combined extracts were washed with water and brine, dried and concentrated to an oil which was purified by FCC eluting with ethyl acetate/triethylamine (99:1) followed by ethyl acetate/methanol/triethylamine (90:10:1) to give the title compound as an orange oil (620 mg), t.l.c. (ethyl acetate/methanol/triethylamine 80:20:1) Rf 0.66.

EXAMPLE 1

N-[2-Hydroxy-5-[1-hydroxy-2-[[6-[[6-(2-pyridinyl)hexyl]oxy]hexyl]amino]ethyl]phenyl]methanesulphonamide, benzoate (salt)

A solution of N-[5-(bromoacetyl)-2-(phenylmethoxy)phenyl]methanesulphonamide (1.80 g), N-[6-[[6-(2-pyridinyl)hexyl]oxy]-hexyl]benzenemethanamine (1.5 g) and DEA (1.05 g) in dichloromethane (40 ml) was left to stand for 24 h. The solvent was evaporated and the residual oil in ethanol (100 ml) was hydrogenated over pre-reduced 10% palladium on charcoal (50% aqueous paste, 0.8 g) and 5% platinum on charcoal (0.9 g), with one change of catalyst. The reaction mixture was filtered (hyflo) and the solvent was evaporated. The residual foam was purified by FCC eluting with System A (80:20:2) to give an oil (0.81 g) which was dissolved in methanol (20 ml) and treated with benzoic acid (195 mg) in methanol (20 ml). The solution was concentrated and the residual foam was triturated with diethyl ether to give the title compound as a white solid (0.85 g) m.p. 93°–95°.

Analysis Found: C,62.5; H,7.7; N,6.5. $C_{26}H_{41}N_3O_5S.C_7H_6O_2$ requires C,62.9; H,7.5; N,6.7%.

EXAMPLE 2

N-[2-Hydroxy-5-[1-hydroxy-2-[[6-[4-(2-quinolinyl)butoxy]hexyl]amino]ethyl]phenyl]methanesulphonamide, benzoate salt (1:1)

A mixture of 2-[4-[(6-bromohexyl)oxy]butyl]quinoline (900 mg), N-[5-(2-amino-1-hydroxyethyl)-2-hydroxyphenyl]methanesulphonamide (800 mg) and DEA (0.52 ml) in DMF (50 ml) was heated at 100° for 4 h, cooled, and the solvent evaporated in vacuo. The residue was purified by FCC eluting with System A (39:10:1) and (34:15:1). A solution of the resulting product in methanol (10 ml) was treated with benzoic acid (61.3 mg), the solution evaporated in vacuo and triturated with dry ether (×2) to afford the title compound as a fawn powder (250 mg) m.p. 155°–157°.

Analysis Found: C,63.5; H,7.0; N,6.5. $C_{28}H_{39}N_3O_5S.C_7H_6O_2. 0.5H_2O$ Requires: C,63.6; H,7.0; N,6.4%

EXAMPLE 3

4-Hydroxy-$\alpha^1$-[[[6-2-(2-quinolinyl)ethoxy]hexyl]amino]methyl]-1,3-benzenedimethanol, benzoate salt (1:1)

2-[2-[(6-Bromohexyl)oxy]ethyl]quinoline (0.90 g) in DMF (10 ml) was added dropwise to a solution of $\alpha^1$-(aminomethyl)-4-hydroxy-1,3-benzene dimethanol (0.86 g) and DEA (0.56 ml) in DMF (30 ml). The solution was heated at 90°–100° under nitrogen for 1 h., cooled and DMF removed in vacuo. The residual gum was purified by FCC eluting with System A (39:10:1) and (34:15:1). A solution of the resulting gum in methanol (10 ml) was treated with benzoic acid (0.26 g), evaporated in vacuo and the residue triturated with dry ether (×3) to give the title compound as a cream solid (621 mg), t.l.c. (System A 39:10:1) Rf 0.14.

Analysis Found: C,69.6; H,7.4; N,4.7. $C_{26}H_{34}N_2O_4.C_7H_6O_2.0.25C_4H_{10}O.0.5H_2O$ requires C,69.4; H,7.45; N,4.8%.

Examples 4 and 5 were prepared in a similar manner from $\alpha^1$-(aminomethyl)-4-hydroxy-1,3-benzenedimethanol (Compound A) and the appropriate bromo compound.

EXAMPLE 4

4-Hydroxy-$\alpha^1$-[[[6-[3-(3-pyridinyl)propoxyl]hexyl]amino]methyl]-1,3-benzenedimethanol, (E)-butenedioate (salt) (2:1)

From Compound A (3.6 g) and 3-[3-[(6-bromohexyl)oxy]propyl]pyridine (3.0 g). FCC eluting with System A (75:25:2) gave a yellow oil (1.5 g). The oil (1.0 g) in methanol (10 ml) was treated with a solution of fumaric acid (160 mg) in methanol. The solvent was evaporated and the residual oil was triturated several times with ether and dried under vacuum to give the title compound as a yellow foam (860 mg), t.l.c. (System A 80:20:2) Rf 0.12.

Analysis Found: C,64.4; H,7.8; N,5.7. $C_{23}H_{34}N_2O_4.0.5C_4H_4O_4.0.22$ $H_2O$ requires C,64.6; H,7.9; N,6.0%.

EXAMPLE 5

4-Hydroxy-$\alpha^1$-[[[6-[4-(2-quinolinyl)butoxy]hexyl]amino]methyl]-1,3-benzenedimethanol From Compound A (0.8 g) and 2-[4-[(6-bromohexyl)oxy]butyl]quinoline (1.08 g). The product obtained from FCC, eluting with System A (39:10:1), was dissolved in a mixture of ethyl acetate (200 ml) and dichloromethane (50 ml) and washed with 2M sodium carbonate solution (100 ml), brine (100 ml), dried and evaporated in vacuo. Trituration of the resultant gum with ether (×2) afforded the title compound as a colourless solid (586 mg), m.p. 104°–106°.

Analysis Found: C,71.9; H,8.3; N,5.8; $C_{28}H_{38}N_2O_4$ requires C,72.1; H,8.2; N,6.0%

EXAMPLE 6

4-Hydroxy-α¹-[[[6-[3-(2-pyridinyl)propoxy]hexyl]amino]methyl]-1,3-benzenedimethanol, (E)-butenedioate (salt) (2:1)

1-[4-Hydroxy-3-(hydroxymethyl)phenyl]-2-[(phenylmethyl)[6-[3-(2-pyridinyl)propoxy]hexyl]amino]ethanone (3.3 g) was hydrogenated over pre-reduced 10% palladium oxide on carbon (500 mg) and 5% platinum on carbon (500 mg) in ethanol (75 ml). The catalyst was removed by filtration through hyflo and the solvent was evaporated to leave an orange oil which was purified by FCC eluting with System A (80:20:2) give a pale yellow oil (1.8 g). A solution of the oil (1.45 g) and fumaric acid (220 mg) in methanol (20 ml) was evaporated to an oil which was triturated several times with dry ether to give the title compound as a cream friable solid (1.45 g), t.l.c. (System A 80:20:2) Rf 0.12.

Analysis Found: C,64.6; H,8.25; N,5.8. $C_{23}H_{34}N_2O_4.0.5C_4H_4O_4.0.25H_2O$ requires C,64.6; H,7.9; N,6.0%.

EXAMPLE 7

4-Hydroxy-α¹-[[[6-[[6-(2-pyridinyl)hexyl]oxy]hexyl]amino]methyl]-1,3-benzenedimethanol A solution of 1-[4-hydroxy-3-(hydroxymethyl)phenyl]-2-[[6-[[6-(2-pyridinyl)hexyl]oxy]hexyl](phenylmethyl)amino]ethanone (1.95 g) in ethanol (50 ml) was hydrogenated over pre-reduced 10% palladium on charcoal (50% aqueous paste, 200 mg) and 5% platinum on charcoal (200 mg), with one change of catalyst. The reaction mixture was filtered (hyflo) and the solvent was evaporated. The residual oil was purified by FCC eluting with System A (80:20:2) to give a semi-solid which on trituration with diethyl ether gave the title compound as a cream solid (0.6 g) m.p 68°-70°.

Analysis Found: C,69.4; H,9.1; N,6.1. $C_{26}H_{40}N_2O_4.0.3H_2O$ requires C,69.4; H,9.1; N,6.2%.

EXAMPLE 8

5-[1-Hydroxy-2-[[6-[[6-(2-pyridinyl)hexyl]oxy]hexyl]amino]ethyl]-1,3-benzenediol (E)-butenedioate (salt) (2:1)

A solution of 3,5-bis(phenylmethoxy)-α-[[(phenylmethyl)[6-[[6-(2-pyridinyl)hexyl]oxy]hexyl]amino]methyl]benzenemethanol (1.97 g) in ethanol (25 ml) was hydrogenated over 10% pre-reduced on charcoal (200 mg). The reaction mixture was filtered (hyflo) and the filtrate was evaporated. The residual oil (1.14 g) in methanol (5 ml) was treated with (E)-butenedioic acid (154 mg) in methanol (5 ml) and the solution was concentrated. The resultant solid was triturated with diethyl ether to give the title compound as a grey solid (1.05 g) m.p. 140°-141°.

Analysis Found: C,65.3; H,8.3; N,5.5. $C_{25}H_{38}N_2O_4.0.5C_4H_4O_4.0.4H_2O$ requires C,65.4; H,8.3; N,5.6%.

EXAMPLE 9

N-[2-Hydroxy-5-[1-hydroxy-2-[[6-[[6-(2-quinolinyl)hexyl]oxy]hexyl-amino]ethyl]phenyl]methanesulphonamide, benzoate salt From [5-[2-amino-1-hydroxyethyl]-2-hydroxyphenyl]methanesulphonamide (1.60 g) and 2-[6-[(6-bromohexyl)oxy]hexyl] quinoline (1.70 g). The product was obtained according to the method of Example 2 and was purified by FCC eluting with System A (80:20:1) to give a pale brown oil. This oil was treated with benzoic acid (0.23 g) in methanol (25 ml), evaporated in vacuo and triturated with diethyl ether to give the title compound as a pale brown solid (1.05 g), m.p. 89°-93°.

Analysis Found: C,63.8; H,7.6; N,6.1. $C_{30}H_{43}N_3O_5S.C_7H_6O_2.H_2O$ requires C,63.7; H,7.4; N,6.0%.

EXAMPLE 10

4-Hydroxy-α¹-[[[6-[3-(3-hydroxy-2-pyridinyl)propoxy]hexyl]amino]methyl]-1,3-benzenedimethanol 1-[4-Hydroxy-3-(hydroxymethyl)phenyl]-2-[[6-[3-[3-(phenylmethoxy)-2-pyridinyl]propoxy]hexyl](phenylmethyl)amino]ethanone (600 mg) was hydrogenated in ethanol (20 ml) over pre-reduced 10% palladium oxide on carbon (50% aqueous paste, 60 mg) and 5% platinum on carbon (60 mg) for 72 h. The catalyst was removed by filtration through hyflo and the ethanol was evaporated. The residual oil was purified by FCC eluting with ethyl acetate/triethylamine (99:1) followed by ethyl acetate/methanol/triethylamine (80:20:1) to give the title compound as a hydroooopio foam (260 mg), t.l.c. (ethyl acetate/methanol/triethylamino 80:20:1) Rf 0.05.

Analysis Found: C,59.5; H,7.6; N,5.5. $C_{23}H_{34}N_2O_5.90.5CHCl_3$ requires C,59.0; H,7.4; N,5.9%.

The following are examples of suitable formulations of compounds of the invention. The term 'active ingredient' is used herein to represent a compound of the invention.

| Tablets (Direct Compression) | |
|---|---|
| | mg/tablet |
| Active ingredient | 2.0 |
| Microcrystalline cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

The tablets may be film coated with suitable film forming materials, such as hydroxypropylmethylcellulose, using standard techniques. Alternatively, the tablets may be sugar coated.

| Metered Dose Pressurised Aerosol (Suspension Aerosol) | | |
|---|---|---|
| | mg/metered dose | Per can |
| Active ingredient micronised | 0.100 | 26.40 mg |
| Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The oleic acid is mixed with the trichlorofluoromethane at a temperature of 10°-15° C. and the micronised drug is mixed into the solution with a high shear mixer. The suspension is metered into aluminium aerosol cans and suitable metering valves delivering 85 mg of suspension are crimped onto the cans and the dichlorodifluoromethane is pressure filled into the cans through the valves.

| Inhalation Cartridges | |
|---|---|
| | mg/cartridge |
| Active ingredient micronised | 0.200 |
| Lactose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents in the cartridges are administered using a powder inhaler such as the Glaxo Rotahaler.

We claim:

1. A compound of the formula (I)

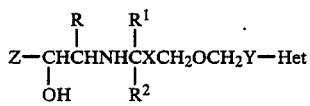

and physiologically acceptable salts and hydrates thereof,
wherein Z represents the group

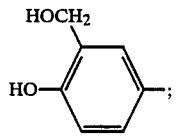

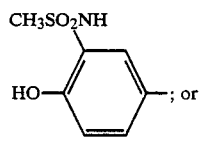

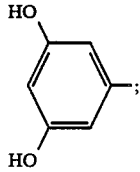

X represents a $C_{1-7}$ alkylene chain, and Y represents a $C_{1-6}$ alkylene chain with the proviso that the sum total of carbon atoms in the chains X and Y is between 5 and 10;

R represents a hydrogen atom;
$R^1$ and $R^2$ each represent a hydrogen atom; and
Het represents a quinolyl or pyridyl group, and the group Het may optionally be substituted by a hydroxy group.

2. A compound according to claim 1 in which X represents —(CH$_2$)$_4$— and Y represents —(CH$_2$)$_3$— or —(CH$_2$)$_5$—.

3. N-[2-hydroxy-5-[1-hydroxy-2-[[6-[[6-(2-pyridinyl)-hexyl]oxy]hexyl]amino]ethyl]phenyl]methanesulphonamide,
N-[2-hydroxy-5-[1-hydroxy-2-[[6-[[4-(2-pyridinyl)-butoxy]-hexyl]amino]ethyl]phenyl]methanesulphonamide,
4-hydroxy-α$^1$-[[[6-[[6-(2-pyridinyl)hexyl]oxy]hexyl]amino]-methyl]-1,3-benzenedimethanol,
N-[2-hydroxy-5-[1-hydroxy-2-[[6-[[6-(2-quinolinyl)-hexyl]oxy]hexyl]amino]ethyl]phenyl]methanesulphonamide, or a physiologically acceptable salt or hydrate thereof.

4. A pharmeceutical composition for therapy or prophylaxis of a disease associated with reversible airways obstruction such as asthma or chronic bronchitis, which comprises an effective amount of alleviate said disease of at least one compound of formula (I) as defined in claim 1 or a physiologically acceptable salt or hydrate thereof, together with a physiologically acceptable carrier or excipient.

* * * * *